US00PP31213P2

(12) United States Plant Patent
Van Swieten

(10) Patent No.: US PP31,213 P2
(45) Date of Patent: Dec. 10, 2019

(54) ***PHALAENOPSIS* ORCHID PLANT NAMED 'PHALFLOXIM'**

(50) Latin Name: ***Phalaenopsis* hybrid**
Varietal Denomination: PHALFLOXIM

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,442

(22) Filed: Nov. 16, 2018

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 6/62
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALFLOXIM', particularly characterized by having light reddish-purple flowers with red-purple lips, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFLOXIM'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFLOXIM'.

The new *Phalaenopsis* plant is a product of a planned breeding program conducted by the inventor in Bleiswijk, The Netherlands. The objective of this breeding program was to create a new *Phalaenopsis* plant with numerous attractive light reddish-purple flowers with red-purple lips, suitable for potted plant production.

The new *Phalaenopsis* plant 'PHALFLOXIM' is a result of cross-pollination made by the inventor in February 2006 in Bleiswijk, The Netherlands, of the proprietary female, or seed parent, *Phalaenopsis* hybrid '14261-01' (unpatented) with the proprietary male, or pollen parent, *Phalaenopsis* hybrid '22715-05' (unpatented).

The new *Phalaenopsis* was selected by the inventor as a single plant within the progeny of the stated cross-pollination in a controlled greenhouse in Bleiswijk, The Netherlands, in April 2009. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALFLOXIM' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALFLOXIM' as a new and distinct variety of *Phalaenopsis* plant:

1) Light reddish-purple flowers with red-purple lips;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in October 2018. Colors in the photographs may differ from the color values cited in the detailed botanical description, which accurately describe the actual colors of the new variety.

DESCRIPTION OF THE NEW VARIETY

Figure 1:
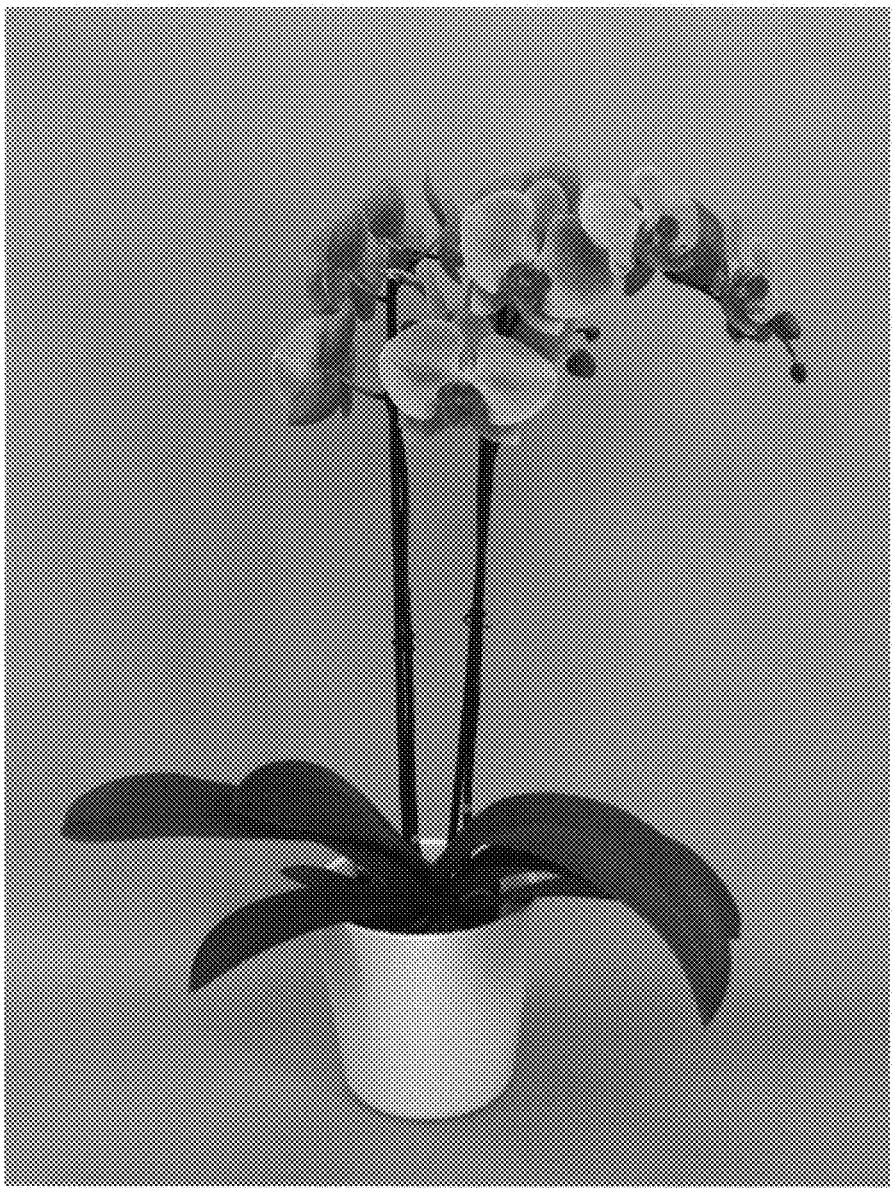
FIG. 1 shows the overall plant habit, including blooms, buds and foliage of 'PHALFLOXIM'.
Figure 2:
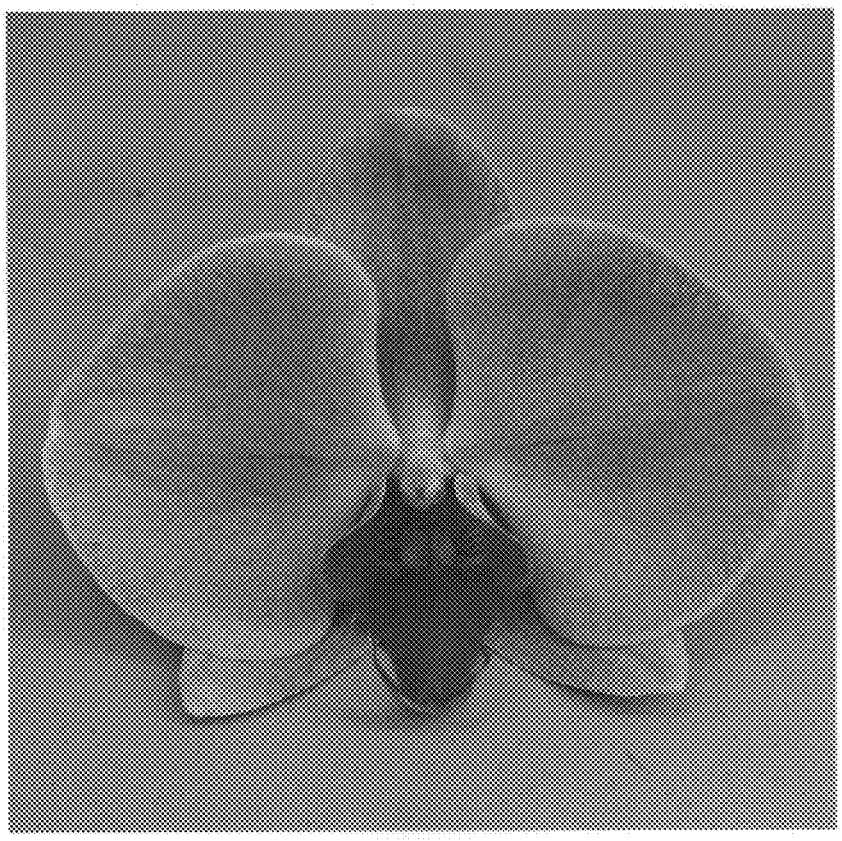
FIG. 2 shows a close-up of a flower of 'PHALFLOXIM'.
Figure 3:
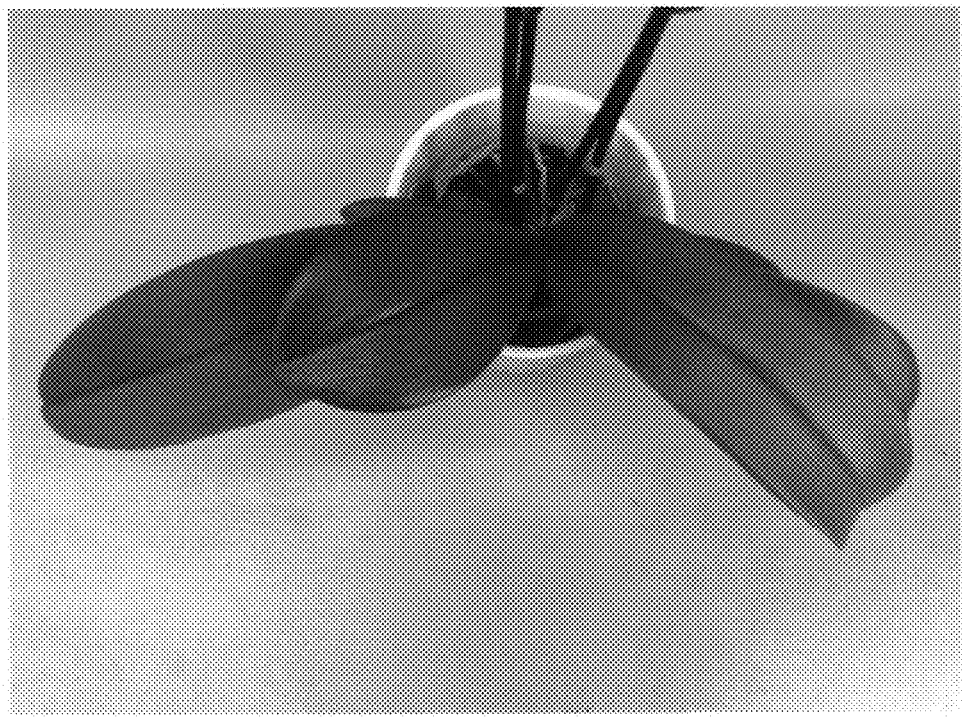
FIG. 3 shows an overhead view of the leaves of 'PHALFLOXIM'.

The following detailed description sets forth the distinctive characteristics of 'PHALFLOXIM'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in October 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12 centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFLOXIM'.

Parentage:

*Female parent*.—*Phalaenopsis* cultivar '14261-01' (unpatented).

*Male parent*.—*Phalaenopsis* cultivar '22715-05' (unpatented).

Propagation:

*Type*.—Meristem tissue culture.

Roots:

*Root description*.—Greyed-green (RHS 190B/C) colored roots with branching lateral roots having red-purple (RHS N77B to N77C) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with raceme to panicle inflorescence.

*Height* (*from soil level to top of inflorescence*).—Approximately 53.0 cm to 58.0 cm.

*Width* (*measured from leaf tips*).—About 37.0 cm to 40.0 cm.

*Vigor*.—Strong.

Leaves:

*Mature leaves*.—Quantity per plant: 7 to 9 leaves are produced before flowering. Length (fully expanded): 22.0 cm to 27.0 cm. Width: 7.0 cm to 8.0 cm. Shape: Oblong. Base shape: Moderately elongated to very elongated. Apex: Obtuse unequal. Leaf blade angle with the petiole (measured from the horizontal position): Between 30 degrees and 40 degrees. Leaf margin: Entire. Color: Upper surface: RHS 146A. Lower surface: RHS 146B with dark red edge (RHS 187A). Texture (upper surface): Rough. Thickness: 2.1 mm to 2.4 mm. Venation: Pattern: Parallel. Color of the midvein: Upper surface: RHS 146A. Lower surface: RHS 146B and diluting dark red (RHS 187A).

Peduncle:

*Quantity per plant*.—1 to 3.

*Number of flowers per peduncle*.—10 to 16.

*Length*.—53.0 cm to 58.0 cm.

*Diameter*.—5.3 mm to 5.8 mm.

*Strength*.—Strong.

*Aspect*.—Upright to slightly pendant.

*Texture*.—Smooth.

*Color*.—Brown (RHS 200A).

*Internode length*.—4.5 cm to 5.5 cm.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 250.0 mm to 300.0 mm.

*Flowering time*.—First flowers can be expected 10 to 11 months after planting in a 12 cm (diameter) pot.

*Flower*.—Height: 75.0 mm to 80.0 mm. Diameter: 97.0 mm to 102.0 mm. Depth of lip: 27.0 mm to 29.0 mm.

*Flower longevity*.—On the plant: 7 to 12 weeks.

*Fragrance*.—Absent.

*Flower bud*.—Average size: Large. Length: 24.0 mm to 26.0 mm. Width: 21.0 mm to 23.0 mm. Shape: Egg shaped. Color: Purplish-red (RHS N77B).

*Petals*.—Arrangement: Open/free. Shape: Semi-circular. Apex: Rounded to slightly emarginated asymmetric. Margin: Entire. Length (from base to tip): 48.0 mm to 50.0 mm. Width: 58.0 mm to 60.0 mm. Color (when fully opened): Upper surface: Basic color: Light purple (RHS 76A). Over color: Reddish-purple shade (between RHS N78B and N78C). Lower surface: Basic color: Very light purple (RHS 76B). Over color: Reddish-purple (RHS N78B) at the base and purplish-pink (RHS N78C) toward tip.

*Dorsal sepal*.—Shape: Elliptic. Apex: Obtuse emarginated. Margin: Entire. Length (from base to tip): 48.0 mm to 50.0 mm. Width: 32.0 mm to 34.0 mm. Color (when fully opened): Upper surface: Basic color: Light purple (RHS 77D). Over color: Reddish-purple shade (RHS N78B). Lower surface: Basic color: Light reddish-purple (RHS N78D). Over color: Reddish-purple (RHS N78B).

*Lateral sepals*.—Shape: Ovate. Apex: Obtuse asymmetric. Margin: Entire. Length (from base to tip): 49.0 mm to 51.0 mm. Width: 27.0 mm to 29.0 mm. Color (when fully opened): Upper surface: Basic color: Light reddish-purple (RHS N78D). Over color: Slightly light yellow-green (RHS 145D) at the base; dotted (RHS 184A). Lower surface: Basic color: Purplish-pink (RHS N78C). Over color: Red (RHS 183D) and reddish-purple venation (RHS N78B) toward the tip.

*Labellum* (*lip*).—Whiskers: Present. Length of whiskers: 17.0 mm to 19.0 mm. Color of whiskers: Reddish-purple (RHS N78A) with white margin (RHS NN155C) and light greenish-yellow tip (RHS 8C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 21.0 mm to 23.0 mm. Width: 16.0 mm to 18.0 mm. Color: White (RHS NN155C) at the base with dark red stripes (RHS 183B); brownish-orange (RHS N170A) on one side and reddish-purple (RHS N78A to N78B) toward other side with very light purple margin (RHS 76B).

*Apical lobe*.—Shape: Triangular to ovate. Margin: Entire. Length: 23.0 mm to 25.0 mm. Width: 22.0 mm to 24.0 mm. Color: Brown-reddish-orange (RHS 172A to 172B) at the base and reddish-purple (RHS N78B) toward whiskers.

*Callus*.—Average size: Medium to large. Height: 7.0 mm to 8.0 mm. Length: 7.0 mm to 8.0 mm. Width: 4.0 mm to 5.0 mm. Color: Yellow (RHS 9A); dotted (RHS 183B).

Reproductive organs:

*Column*.—Length: 9.0 mm to 11.0 mm. Diameter: 5.7 mm to 6.0 mm. Color: Light purple (RHS 76A) at the base with reddish-purple region (RHS N78B) toward the tip.

*Pollinia*.—Quantity: 2. Diameter: 1.0 mm to 1.2 mm. Color: Orange (RHS 25A).

*Ovary*.—Length: 10.0 mm to 12.0 mm. Diameter: 2.5 mm to 2.8 mm. Color: Light purple (RHS 186D) toward the flower.

*Pedicel*.—Length: 40.0 mm to 42.0 mm. Diameter: 2.9 mm to 3.2 mm. Color: Mix of light green and red (RHS 146C and 182B) at the base; light purple (RHS 186D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFLOXIM' differs from female parent plant '14261-01' (unpatented) in that 'PHALFLOXIM' has flowers with an upper surface basic color of light purple (RHS 76A) and a shaded pattern, whereas '14261-01' has flowers with an upper surface basic color of very light purple (RHS 76C) and a shaded and striped pattern. Additionally, 'PHALFLOXIM' has columns that are light purple (RHS 76A) at the base with a reddish-purple region (RHS N78B) toward the tip, whereas '14261-01' has columns that are purplish-pink (RHS N78C).

'PHALFLOXIM' differs from male parent plant '22715-05' (unpatented) in that 'PHALFLOXIM' has flowers with an upper surface basic color of light purple (RHS 76A) and a shaded pattern, whereas '22715-05' has flowers with an upper surface basic color of reddish-purple (RHS N78A to N78B) and an edged pattern. Additionally, 'PHALFLOXIM' has columns that are light purple (RHS 76A) at the base with a reddish-purple region (RHS N78B) toward the tip, whereas '22715-05' has columns that are reddish-purple (RHS N78A to N78B).

'PHALFLOXIM' is most similar to the commercial *Phalaenopsis* plants named 'PHALCIMEI' (U.S. Plant Pat. No. 27,200) and 'PHALDESBIM' (U.S. Plant Pat. No. 27,671). 'PHALFLOXIM' differs from the commercial variety 'PHALCIMEI' in that 'PHALFLOXIM' has obtuse unequal leaf apexes, whereas 'PHALCIMEI' has unequal mucronate leaf apexes. Additionally, 'PHALFLOXIM' has smaller flowers, shorter whiskers and shorter dorsal sepals than 'PHALCIMEI'.

'PHALFLOXIM' differs from the commercial variety 'PHALDESBIM' in that 'PHALFLOXIM' has petals with an open/free arrangement, whereas 'PHALDESBIM' has petals that are almost touching. Additionally, 'PHALFLOXIM' has larger flowers, longer leaves and longer dorsal sepals than 'PHALDESBIM'.

I claim:

1. A new and distinct variety of *Phalaenopsis* plant named 'PHALFLOXIM', substantially as described and illustrated herein.

* * * * *